US007154109B2

(12) United States Patent
Stivers

(10) Patent No.: US 7,154,109 B2
(45) Date of Patent: Dec. 26, 2006

(54) METHOD AND APPARATUS FOR PRODUCING ELECTROMAGNETIC RADIATION

(75) Inventor: Alan R. Stivers, Palo Alto, CA (US)

(73) Assignee: Intel Corporation, Santa Clara, CA (US)

( * ) Notice: Subject to any disclaimer, the term of this patent is extended or adjusted under 35 U.S.C. 154(b) by 132 days.

(21) Appl. No.: 10/956,194

(22) Filed: Sep. 30, 2004

(65) Prior Publication Data

US 2006/0066197 A1 Mar. 30, 2006

(51) Int. Cl.
*A61N 5/06* (2006.01)
*G01J 3/10* (2006.01)
*H05G 2/00* (2006.01)

(52) U.S. Cl. .............................. 250/504 R; 250/504 R

(58) Field of Classification Search ............. 250/504 R
See application file for complete search history.

(56) References Cited

U.S. PATENT DOCUMENTS

2004/0105082 A1* 6/2004 Koshelev et al. ............. 355/53

* cited by examiner

*Primary Examiner*—Jack Berman
*Assistant Examiner*—Jennifer Yantorno
(74) *Attorney, Agent, or Firm*—Blakely, Sokoloff, Taylor & Zafman LLP

(57) ABSTRACT

According to one aspect of the invention, a method and apparatus for producing electromagnetic radiation is provided. The apparatus may include a chamber wall enclosing a plasma emission chamber to contain a plasma emission gas. A first electrode may be within the plasma emission chamber. At least one second electrode may within the plasma emission chamber. The at least one second electrode may be rotatable about an axis thereof and positioned within the plasma emission chamber such that when a voltage is applied across the first electrode and the at least one second electrode, a plasma is generated between the first electrode and the at least one second electrode.

39 Claims, 6 Drawing Sheets

METHOD AND APPARATUS FOR PRODUCING ELECTROMAGNETIC RADIATION

BACKGROUND OF THE INVENTION

1). Field of the Invention

Embodiments of this invention relate to a method and apparatus for producing electromagnetic radiation, particularly for use in semiconductor substrate processing.

2). Discussion of Related Art

Integrated circuits are formed on semiconductor wafers. The wafers are then sawed (or "singulated" or "diced") into microelectronic dice, also known as semiconductor chips, with each chip carrying a respective integrated circuit. Each semiconductor chip is then mounted to a package, or carrier, substrate. Often the packages are then mounted to a motherboard, which may then be installed into a computing system.

Numerous steps may be involved in the creation of the integrated circuits, such as the formation and etching of various semiconductor, insulator, and conductive layers. Before the various layers may be etched, a layer of light-sensitive photoresist is formed on the substrate to protect the portions of the substrate that are not to be etched.

Machines referred to as photolithography steppers are used to expose the desired pattern in the photoresist layer. In order to achieve the desired pattern, light, or electromagnetic radiation, is directed through a reticle, or "mask," and focused onto the substrate.

As the features on the semiconductor substrates become smaller, shorter wavelength electromagnetic radiation is required to expose the photoresist. One form of such electromagnetic radiation is known as "extreme ultraviolet" (EUV) light. EUV light is often produced in plasma chambers by applying a voltage across a cathode and an anode, which are held within a plasma emission gas, such as xenon.

As the plasma is generated between the cathode and anode, tremendous heat often builds up on the anode, which can lead to the anode becoming permanently damaged, such as by melting.

BRIEF DESCRIPTION OF THE DRAWINGS

Embodiments of the invention are described by way of example with reference to the accompanying drawings, wherein.

DETAILED DESCRIPTION OF THE INVENTION

In the following description, various aspects of the present invention will be described, and various details set forth in order to provide a thorough understanding of the present invention. However, it will be apparent to those skilled in the art that the present invention may be practiced with only some or all of the aspects of the present invention, and the present invention may be practiced without the specific details. In other instances, well-known features are admitted or simplified in order not to obscure the present invention.

It should be understood that FIGS. 1–5 are merely illustrative and may not be drawn to scale.

FIG. 1 to FIG. 5 illustrate a method and apparatus for producing electromagnetic radiation according an embodiment of the present invention. The apparatus may include a chamber wall enclosing a plasma emission chamber to contain a plasma emission gas. A first electrode may be connected to the chamber wall within the plasma emission chamber. At least one second electrode may be connected to the chamber wall within the plasma emission chamber. The at least one second electrode may be rotatable about an axis thereof and positioned within the plasma emission chamber such that when a voltage is applied across the first electrode and the at least one second electrode, a plasma is generated between the first electrode and the at least one second electrode.

Figure 1:
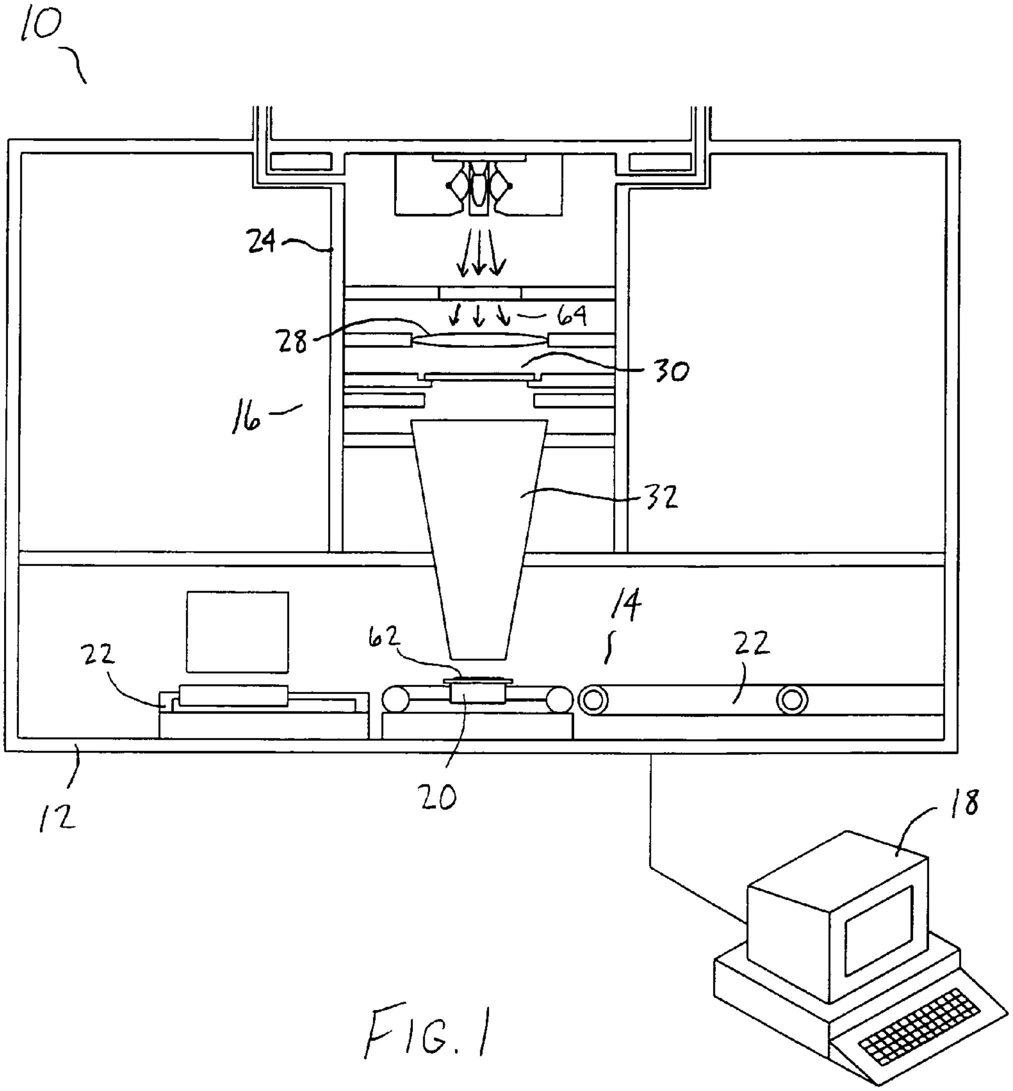
FIG. 1 is a cross-sectional schematic view of a semiconductor substrate processing system, including an electromagnetic radiation source.

FIG. 1 illustrates a semiconductor processing apparatus, or a photolithographic stepper 10, according to an embodiment of the present invention. The stepper 10 may include a frame 12, a substrate transport subsystem 14, an exposure subsystem 16, and a computer control console 18.

The substrate transport subsystem 14 may be attached to and located at a lower portion of the frame 12 and may include a substrate support 20 and a substrate track 22. The substrate support 20 may be sized to support semiconductor substrates, such as wafers with diameters of, for example, 200 or 300 mm. Although not illustrated in detail, the substrate support 20 may include various actuators and motors to move the substrate support 20 in an X/Y coordinate system which may be substantially perpendicular to the sheet, or page, on which FIG. 1 is shown. The substrate track 22 may include various components to place a semiconductor substrate onto the substrate support 20 and remove the semiconductor substrate therefrom.

The exposure subsystem 16 may be connected to the frame and suspended substantially over the substrate support 20. The exposure subsystem 16 may include an electromagnetic radiation source 24, a collector 28, a reticle 30, and imaging optics 32.

Figure 2:
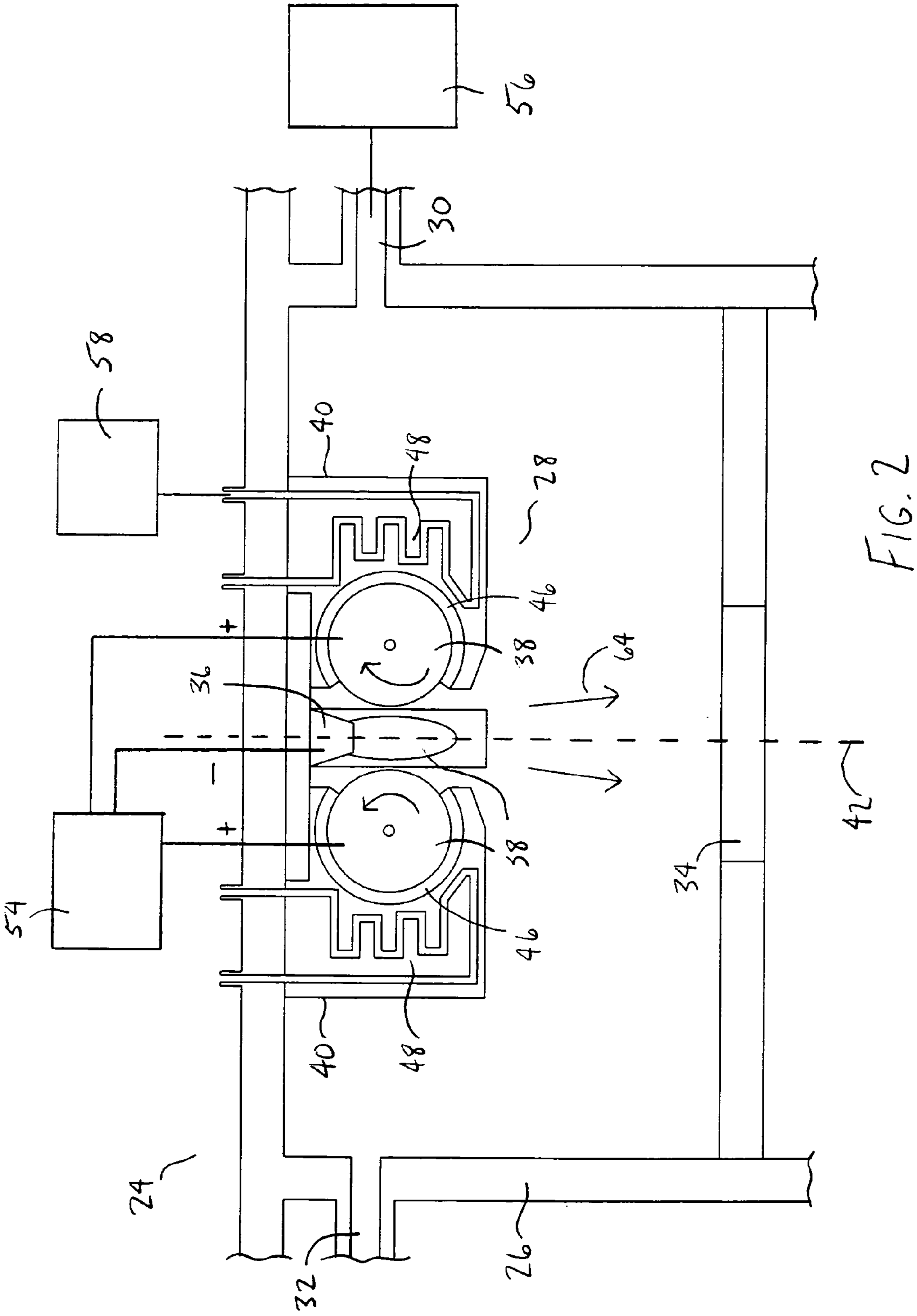
FIG. 2 is a cross-sectional schematic view of the electromagnetic radiation source illustrated in FIG. 1, including an electrode subsystem having a plurality of electrodes.

As illustrated in FIG. 2, the electromagnetic radiation source 24 may be in the form of a plasma emission chamber, or apparatus, and include a chamber wall 26 and an electrode subsystem 28. The chamber wall 26 may be substantially rectangular in cross-section, enclose a plasma emission chamber, and include an inlet 30 and an outlet 32 in opposing side sections thereof. The chamber wall 26 may also include a window 34 located in a central portion of a lower section thereof. The window 34 may have a zirconium plate placed therein, as is commonly understood in the art.

The electrode subsystem 28 may be secured to an upper section of the chamber wall 26, or the frame 12, and may include at least one first electrode 36, and at least one, or a plurality, of second electrodes 38, as well as heat exchangers 40. The first electrode 36 may be a cathode and have a trapezoidal cross-section. The first electrode 36 (hereinafter referred to as "the cathode") may have a central axis 42, which extends through a central portion of the plasma emission chamber, and may be made of a conductive material, such as copper.

Figure 3:
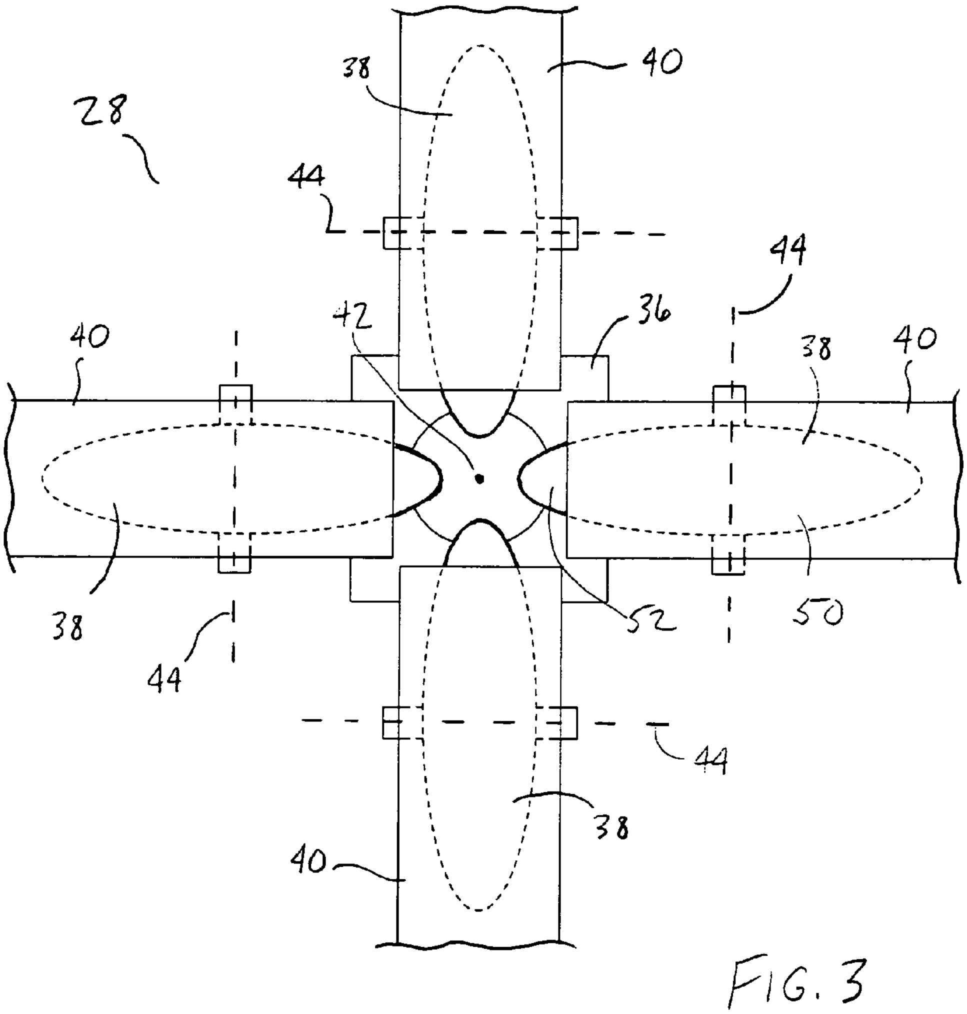
FIG. 3 is a bottom view of the electrode subsystem illustrated in FIG. 2.

The second electrodes 38 (hereinafter referred to as "the anodes), as illustrated in FIGS. 2 and 3, may be substantially disc, or wheel, shaped with a circular outer edge and a substantially elliptical cross-section. Although not illustrated in detail, each anode 38 may be connected to the chamber wall 26, or the frame 12, to rotate about a central axis 44 thereof. As shown in the embodiment illustrated in FIGS. 2 and 3, there may be, for example, four anodes 38 symmetrically arranged about the central axis 42 of the cathode 36.

The anodes 38 may be positioned so that the central axis 44 of each anode 38 is orthogonal to the central axis 42 of the cathode 36. The anodes 38 may be made of an electrically conductive material, with a first thermal conductivity, such as a titanium alloy. The anodes 38 may also be made of other metals with high melting temperatures, such as molybdenum and tungsten.

Although not illustrated, the plasma emission chamber 24 may also include actuators connected to the anodes 38 to rotate the anodes 38 about the central axes 44 thereof.

Still referring to FIGS. 2 and 3, the heat exchangers 40 may include an anode portion 46 and a cooling portion 48. The anode portion 46 of each heat exchanger 40 may include an anode chamber sized and shaped to fit around one of the anodes 38 so that each anode 38 is divided into a portion covered by the heat exchanger 40 and an exposed portion 52. The exposed portion 52 of each anode 38 may be a first distance from the cathode 36 (or the central axis 42 thereof), and the covered portion 50 may be a second distance, greater than the first distance, from the cathode 36. In the embodiment illustrated in FIG. 3, the exposed portion 52 of each anode 38 may be positioned directly between the central axis 42 of the cathode and the covered portion 50 of the same anode 38. The first distance may be less than 1 cm. The cooling portion 48 of each heat exchanger 48 may include a fluid channel therethrough. The heat exchangers 40 may be made of a thermally conductive material, with a second thermal conductivity, such as copper. The second thermal conductivity may be greater than the first thermal conductivity.

The heat exchangers 40 may connect each anode 38 to the chamber wall 26. The heat exchangers 40 may be rectangular in shape and have a rectangular cross-section when viewed in a direction parallel to the central axis 42 of the cathode 36.

As illustrated in FIG. 2, the stepper 10 may further include a power supply 54, a plasma emission gas supply 56, and a cooling fluid supply 58. The power supply 54 may include a plurality of electrodes electrically connected to the cathode 36 and the anodes 38. The plasma emission gas supply 56 may contain a plasma emission gas, such as xenon, lithium, or tin vapor and may be in fluid communication with the inlet 30 of the chamber wall 26. The cooling fluid supply 58 may contain a cooling fluid, such as liquid nitrogen or chilled water, and may be in fluid communication with the fluid channel within each of the cooling portions 48 of the heat exchangers 40.

Referring again to FIG. 1, the collector 28, the reticle 30, and the imaging optics 32 may be connected to the frame 12 and positioned beneath the electromagnetic radiation source 24. The collector 28 may be in the form of a an optic, as is commonly understood in the art. The reticle 30 may be positioned below the collector 28, may be in the form of "mask," as is commonly understood in the art, and may include a plurality of openings therein. The imaging optics 32 may be positioned below the reticle 30 and, although not illustrated in detail, may include a plurality of lenses of varying shapes and sizes. Although not illustrated as such, the imaging optics 32 may also be positioned above the reticle 30.

The computer control console 18 may be in the form a computer having memory for storing a set of instructions and a processor connected to the memory for executing the instructions, as is commonly understood in the art. The computer control console 18 may be electrically connected to both the substrate transport subsystem 14 and the exposure subsystem 16, as well as all of the various components thereof, and may control and coordinate the various operations of the stepper 10.

In use, a semiconductor substrate 62, such as a wafer having a diameter of, for example, 200 or 300 mm, may be placed on the substrate support 20 by the substrate track 22. The substrate 62 may have a plurality of integrated circuits, divided amongst multiple microelectronic dice, formed thereon and a layer of photoresist deposited over the dice.

Referring to FIG. 2, the plasma emission gas supply 56 may then be activated to deliver a plasma emission gas through the inlet 30 and into the plasma chamber enclosed by the chamber wall 26. The plasma emission gas may be dispersed throughout the chamber such that the plasma emission gas is between and in contact with the cathode 36 and the anodes 38. The power supply 54 may then apply a voltage across the cathode 36 and the anodes 38 of, for example, between 70 and 300 volts (V), while the anodes 38 are rotated about the central axes 44. The anodes 38 may be rotated at a rate of, for example, between 50 and 200 rpm.

As is commonly understood in the art, when the voltage between the anodes 38 and the cathode reaches the "discharge voltage" for the particular plasma gas used, a plasma may be generated between the anodes 38 and the cathode 36. In particular, a plasma may be generated from the plasma gas between the exposed portions 52 of the anodes and the cathode 36. The plasma may emit electromagnetic radiation, such as extreme ultraviolet radiation. The electromagnetic radiation 64 may have a wavelength of, for example, between 2 and 200 nanometers (nm), depending on the particular plasma gas used. In one embodiment, in which xenon gas is used, the electromagnetic radiation 64 may have a wavelength of approximately 13.5 nm.

During the generation of the plasma, the exposed portions 52 of the anodes 38 may be subjected to extreme temperatures, such as over 1000° C. The cooling liquid supply 58 may be activated to supply the cooling liquid, such as liquid nitrogen (at 77° K), through the fluid channel within the cooling portion 48 of each of the heat exchangers 40, and thus cool the heat exchanger 40.

Because of the rotation of the anodes 38, the heat generated during the plasma generation is distributed evenly along the outer edges of the anodes 38. Additionally, the exposed portions 52 of the anodes 38 may be subjected to the high plasma temperatures for only a brief period before being rotated into the anode chamber 46 of the heat exchangers 40. As the exposed portions 52 are rotated into the anode chamber 46, because the thermal conductivity of the heat exchangers 40 may be higher than the thermal conductivity of the anodes 38, and due to the cooling of the heat exchangers 40, heat from the anodes 38 may be transferred to the heat exchangers 40 through conduction and radiation.

Still referring to FIG. 2, the electromagnetic radiation 64 may propagate from the electrode subsystem 28 through the window 34 in the chamber wall 26.

Referring to FIG. 1, the electromagnetic radiation 64 may then propagate from the electromagnetic radiation source 24 into the collector 28. The collector 28 may focus the electromagnetic radiation 64 through the reticle 30 and into the imaging optics 32. The imaging optics 32 may further focus the electromagnetic radiation 64 before the electromagnetic radiation 64 is directed onto the semiconductor substrate 62, where the electromagnetic radiation 64 may expose the layer of photoresist, as is commonly understood in the art.

The wafer support 20 may move the semiconductor substrate 62 in the X/Y coordinate system so that individual sections of the semiconductor substrate 62, which may correspond with one or more of the dice, may be exposed one at a time, as is common understood in the art. When the entire photoresist layer has been exposed, the substrate track 22 may remove the semiconductor substrate 62 from the substrate support 22, and replace it with a second semiconductor substrate to be exposed as described above.

One advantage is that because of the rotation of the anodes during the generation of the plasma, the heat generated is distributed around the anodes, preventing any one portion of the anodes from becoming too hot and becoming permanently damaged. Another advantage is that because the heat exchangers have a thermal conductivity that is higher than the thermal conductivity of the anodes, heat is more easily transferred from the anodes and into the heat exchangers, thus further increasing the cooling of the anodes. A further advantage is that the cooling fluid keeps the temperature of the heat exchangers very low, thus increasing the cooling of the anodes even further. A further advantage is that the heating on bearings within the anodes is minimized thus provided the anodes with improved reliability and longevity. A further advantage is that because of the heat exchanger, there is no need to have a liquid cooling system within the anode itself, thus reducing the costs of manufacturing the anodes.

Figure 4A:
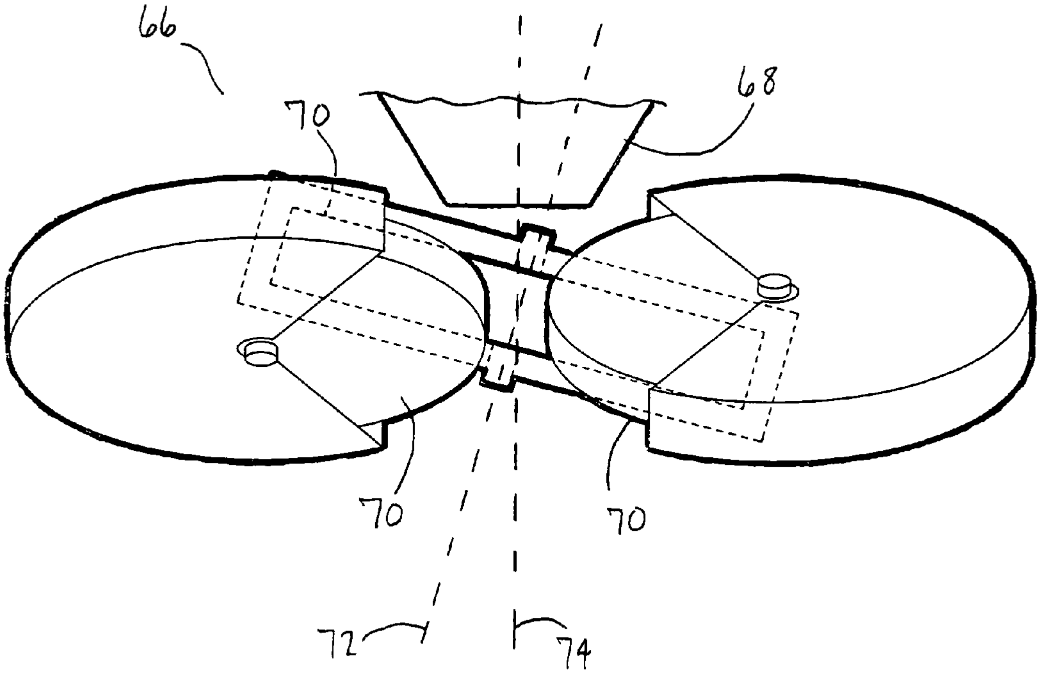
FIG. 4A is a side view of an electrode subsystem according to another embodiment of the invention.
Figure 4B:
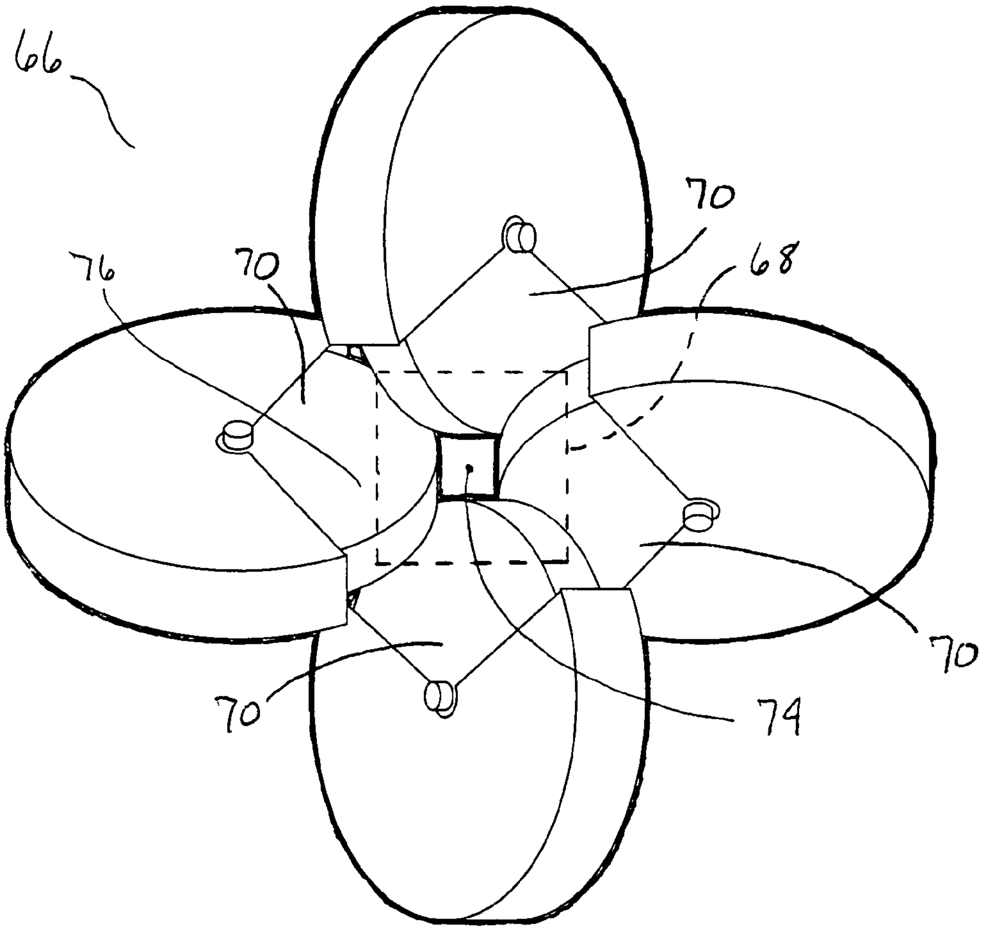
FIG. 4B is a bottom view of the electrode subsystem illustrated in FIG. 4A.

FIGS. 4A and 4B illustrate an electrode subsystem 66 according to another embodiment of the invention. The electrode subsystem 66 may include a cathode 68 and anodes 70, similar to the cathode 36 and anodes 38 illustrated in FIGS. 2 and 3. However, each of the anodes 70 may be "tilted" such that the central axes 72 of the anodes 70 are at an angle to a central axis 74 of the cathode 68, as illustrated in FIG. 4A. Thus, as illustrated in FIG. 4B, exposed portions 76 of the anodes 70, may be "overlapped" such that a portion of each of the anodes 70 is positioned beneath a portion of another anode 70, while another portion of each anode 70 is above a portion of a third anode 70. The electrode subsystem 66 may also include heat exchangers, similar to the heat exchangers 40 illustrated in FIGS. 2 and 3, which are not entirely shown in FIGS. 4A and 4B for clarity. A further advantage of the electrode subsystem 66 is that because of the tilt of the anodes 70, the anodes 70 may be positioned more closely to the cathode 68.

Figure 5:
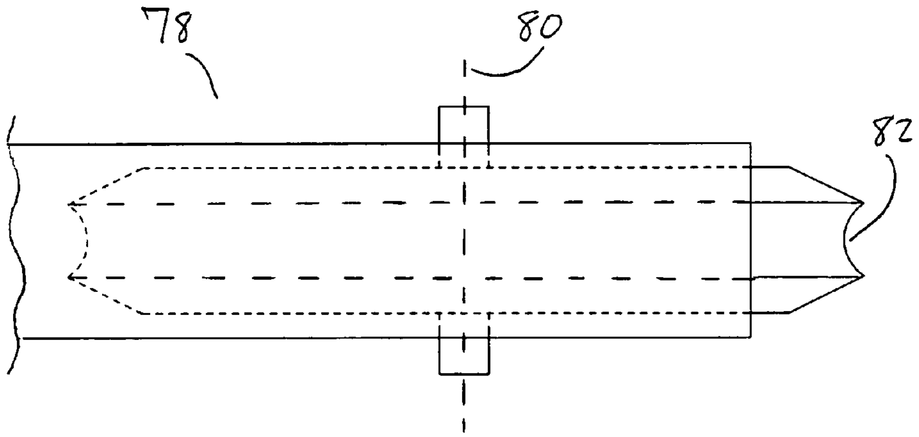
FIG. 5 is a bottom view of an electrode according to another embodiment of the invention.

FIG. 5 illustrates an anode 78 according to another embodiment of the invention. The anode 78 may be similar to the anodes 38 illustrated in FIGS. 2 and 3 and may include a central axis 80 and an outer edge 82. However, as illustrated in FIG. 5, the outer edge 82 may have a depression extending completely around. As such, the shape of the anode 78 may be altered to vary the characteristics of the plasma generation process, as is commonly understood in the art.

Other embodiments may use a different number of anodes, such as six, which may or may not be symmetrically arranged about the central axis of the cathode, or any other axis. The heat exchangers may not be required as the rotation of the electrodes may sufficiently distribute the heat generated across the surface of the electrode to prevent the electrodes from being damaged. The cathode may rotate instead of the anode, or both electrodes may rotate during the plasma generation.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art

What is claimed is:

1. An apparatus comprising:

a chamber wall enclosing a plasma emission chamber to contain a plasma emission gas;

a first electrode within the plasma emission chamber; and at least one second electrode within the plasma emission chamber, the at least one second electrode being rotatable about an axis thereof and being positioned within the plasma emission chamber such that when a voltage is applied across the first electrode and the at least one second electrode, a plasma is generated between the first electrode and the at least one second electrode; and at least one heat exchanger covering at least a portion of the at least one second electrode, wherein an uncovered portion of the at least one second electrode is a first distance from the first electrode and the covered portion of the at least one second electrode is a second distance from the first electrode, the second distance being greater than the first distance.

2. The apparatus of claim 1, wherein the plasma emits electromagnetic radiation.

3. The apparatus of claim 2, wherein the electromagnetic radiation is ultraviolet electromagnetic radiation.

4. The apparatus of claim 3, wherein the ultraviolet radiation has a wavelength of between 2 and 200 nm.

5. The apparatus of claim 4, wherein the at least one second electrode has a circular outer edge and is rotatable about a central axis thereof.

6. The apparatus of claim 5, wherein the at least one heat exchanger is connected to the chamber wall.

7. The apparatus of claim 1, wherein the first electrode is a cathode having a central axis and the at least one second electrode comprises a plurality of anodes being symmetrical positioned about the central axis of the cathode.

8. The apparatus of claim 7, wherein the at least one heat exchanger comprises a plurality of heat exchangers, each heat exchanger covering a portion of the one of the anodes and including a fluid channel.

9. The apparatus of claim 8, wherein the anodes comprise a first conductive material having a first thermal conductivity and the heat exchangers comprise a second conductive material having a second thermal conductivity, the second thermal conductivity being higher than the first thermal conductivity.

10. A semiconductor substrate processing system comprising:

a flame;

a semiconductor substrate support connected to the frame to support a semiconductor substrate;

an electromagnetic radiation source connected to the frame, the electromagnetic radiation source comprising:

a chamber wall enclosing a plasma emission chamber to contain a plasma emission gas;

a first electrode connected to the frame and being within the plasma emission chamber; and at least one second electrode connected to the frame and being within the plasma emission chamber, the at least one second electrode being rotatable about an axis thereof and being positioned within the plasma emission chamber such that when a voltage is applied across did first electrode and the at least one second electrode, a plasma is generated between the first electrode and the at least one second electrode, the plasma emitting electromagnetic radiation;

at least one heat exchanger covering at least a portion of the at least one second electrode; and a reticle connected to the frame and positioned between the electromagnetic radiation source and the substrate support, the electromagnetic radiation to pass through the reticle onto the semiconductor substrate, wherein an uncovered portion of the at least one second electrode is a first distance from the first electrode and the covered portion of the at least one second electrode is a second distance from the first electrode, the second distance being greater than the first distance.

11. The semiconductor substrate processing system of claim 10, wherein the at least one second electrode has a circular outer edge and is rotatable about a central axis thereof.

12. The semiconductor substrate processing system of claim 11, further comprising a plasma emission gas supply in fluid communication with the plasma emission chamber.

13. The semiconductor substrate processing system of claim 12, further comprising a power supply being electrically connected to the first electrode and the at least one second electrode.

14. The semiconductor substrate processing system of claim 13, wherein the electromagnetic radiation source further comprises:

at least one heat exchanger connected to the frame and covering at least a portion of the at least one second electrode.

15. The semiconductor substrate processing system of claim 14, wherein the at least one heat exchanger comprises a fluid channel therethrough.

16. The semiconductor substrate processing system of claim 15, further comprising a cooling fluid supply in fluid communication with the fluid channel through the at least one heat exchanger.

17. The semiconductor substrate processing system of claim 10, wherein the first electrode is a cathode having a central axis and the at least one second electrode comprises a plurality of anodes being symmetrically positioned about the central axis of the cathode.

18. The semiconductor substrate processing system of claim 17, wherein the central axis of each anode is orthogonal to the central axis of the cathode.

19. A method comprising:

placing a first and a second electrode in contact with a plasma emission gas;

applying a voltage across the first electrode and the second electrode such that a plasma is generated between the first and second electrode; and rotating the second electrode during the plasma generation through a heat exchanger covering at least a portion of the second electrode wherein an uncovered portion of the second electrode is a first distance from the first electrode and the covered portion of the second electrode is a second distance from the first electrode, the second distance being greater than the first distance.

20. The method of claim 19, wherein the second electrode has a circular outer edge and the rotation occurs about a central axis thereof.

21. The method of claim 20, wherein the plasma emits electromagnetic radiation.

22. The method of claim 21, wherein the electromagnetic radiation has a wavelength between 2 and 200 nm.

23. The method of claim 22, wherein the plasma emission gas includes at least one of xenon, lithium, and tin vapor.

24. The method of claim 23, further comprising covering a portion of the second electrode with a heat exchanger.

25. The method of claim 24, wherein the heat exchanger further comprises a fluid channel therethrough.

26. The method of claim 25, wherein the second electrode comprises a first conductive material having a first thermal conductivity and the heat exchanger comprises a second conductivity material having a second thermal conductivity, the second thermal conductivity being higher than the first thermal conductivity.

27. An apparatus comprising:

a chamber wall enclosing a plasma emission chamber to contain a plasma emission gas;

a cathode within the plasma emission chamber, the cathode having a central axis: and a plurality of anodes within the plasma emission chamber positioned about the central axis of the cathode, the anodes each being rotatable about a respective axis, the axis of each anode being orthogonal to the central axis of the cathode, the anodes being positioned within the plasma emission chamber such that when a voltage is applied across the cathode and each anode, a plasma is generated between the cathode and the respective anode.

28. The apparatus of claim 27, wherein the plasma emits electromagnetic radiation.

29. The apparatus of claim 27, wherein the anodes have a circular outer edge about the respective axis.

30. The apparatus of claim 29, wherein the circular edge has a circular depression extending around the edge.

31. The apparatus of claim 27, wherein the anodes have a substantially elliptical cross section.

32. The apparatus of claim 27, further comprising a least one heat exchanger connected to the chamber wall and covering at least a portion of an anode.

33. The apparatus of claim 32, wherein an uncovered portion of the anode is a first distance from the cathode and the covered portion of the anode is a second distance from the cathode, the second distance being greater than the first distance.

34. The apparatus of claim 27, wherein the anodes have symmetrically positioned about the cathode.

35. The apparatus of claim 27, wherein the anodes have outer edges and wherein the rotation of the anodes distributes heat around the outer edges of the anodes.

36. A method comprising:

placing a first and a second electrode in contact with a plasma emission gas, the first electrode having a central axis and the second electrode having an axis orthogonal to the central axis;

applying a voltage across the first electrode and the second electrode such that a plasma is generated between the first and second electrode; and rotating the second electrode about its axis during the plasma generation to distribute heat during the plasma generation about the surface of the second electrode.

37. The method of claim 36, wherein the second electrode has a circular outer edge and the heat is distributed around the circular outer edge.

38. The method of claim 37, wherein the second electrode is rotated through a heat exchanger covering at least a portion of the second electrode that is distanced from the first electrode.

39. The method of claim 36, further comprising a plurality of additional second electrodes, each rotatable about an axis orthogonal to the central axis.

* * * * *